(12) United States Patent
Kreh et al.

(10) Patent No.: US 7,327,450 B2
(45) Date of Patent: Feb. 5, 2008

(54) APPARATUS FOR INSPECTION OF A WAFER

(75) Inventors: Albert Kreh, Solms (DE); Henning Backhauss, Wetzlar (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 584 days.

(21) Appl. No.: 10/879,990

(22) Filed: Jun. 30, 2004

(65) Prior Publication Data

US 2005/0001900 A1 Jan. 6, 2005

(30) Foreign Application Priority Data

Jul. 3, 2003 (DE) ................. 103 30 006

(51) Int. Cl.
*G01N 21/00* (2006.01)
(52) U.S. Cl. ................. 356/237.5; 356/237.2
(58) Field of Classification Search ... 356/237.2–237.6
See application file for complete search history.

(56) References Cited

U.S. PATENT DOCUMENTS

| | | | |
|---|---|---|---|
| 5,038,258 A | | 8/1991 | Koch et al. |
| 5,046,847 A | * | 9/1991 | Nakata et al. ............... 356/338 |
| 5,177,559 A | * | 1/1993 | Batchelder et al. ....... 356/237.5 |
| 6,630,996 B2 | * | 10/2003 | Rao et al. ................. 356/237.5 |
| 6,888,627 B2 | * | 5/2005 | Leslie et al. ............. 356/237.2 |
| 7,064,820 B2 | * | 6/2006 | Isozaki et al. ........... 356/237.2 |
| 7,180,585 B2 | * | 2/2007 | Kreh et al. ............... 356/237.2 |
| 7,248,354 B2 | * | 7/2007 | Kreh et al. ............... 356/237.5 |

| | | |
|---|---|---|
| 2003/0117616 A1 | 6/2003 | Nakamura |

FOREIGN PATENT DOCUMENTS

| | | |
|---|---|---|
| DE | 36 06 555 A1 | 7/1989 |
| DE | 39 06 555 A1 | 7/1989 |
| DE | 100 28 201 A1 | 12/2001 |
| WO | WO 02/090952 A1 | 11/2002 |

OTHER PUBLICATIONS

I. Peterson et al., "Lithography Defetcs: Reducing and Managing Yield Killers through Photo Cell Monitoring", Yield Management Solutions, Spring 2000, pp. 17-24.

* cited by examiner

*Primary Examiner*—Layla G. Lauchman
(74) *Attorney, Agent, or Firm*—Foley & Lardner LLP (57) ABSTRACT

The invention concerns an apparatus for inspection of a wafer, encompassing at least two incident-light illumination devices that radiate a respective illuminating light beam which is incident obliquely onto the surface of a wafer to be inspected and respectively defines an illumination axis, an image capture device for capturing an image of the surface in a dark-field arrangement, and a wafer receiving device for receiving the wafer, on whose surface linearly extending features are configured, in a definable orientation. The apparatus is characterized in that the illumination axes are oriented perpendicular to one another, and the apparatus is designed in such a way that a projection of the respective illumination axis onto the surface of the wafer is oriented substantially perpendicular to respective linear features on the surface of the wafer.

With the apparatus, macrodefects can be detected and the quality of the edge profile of features configured on the surface of the wafer can be assessed.

23 Claims, 6 Drawing Sheets

APPARATUS FOR INSPECTION OF A WAFER

CROSS REFERENCE TO RELATED APPLICATIONS

This application claims priority of the German patent application 103 30 006.6 which is incorporated by reference herein.

FIELD OF THE INVENTION

The present invention concerns an apparatus for inspection of a wafer, and concerns in particular an apparatus for the detection of macrodefects and for assessment of the edge profile of features, for example integrated circuits (ICs), that are configured on the wafer.

BACKGROUND OF THE INVENTION

In semiconductor production, wafers are processed sequentially in a plurality of process steps during the production process. With increasing integration density, requirements in terms of the quality of features to be configured on the wafer are rising. It is advantageous for this purpose if the quality even of individual process steps, for example lithography steps, can be dependably assessed during the production process and prior to a subsequent process step. The reason is that if a determination can be made, directly after a process step is performed and before final completion of a production process, that a wafer or the features configured on a wafer are defective, the wafer can be immediately discarded with no need to perform other subsequent process steps. Or the wafer identified as defective can be given special additional treatment until satisfactory quality is achieved. Efficiency and yield in semiconductor processing can thus be improved.

Optical apparatuses are particularly suitable for inspecting the surface of wafers. Optical apparatuses are known that can detect, by image recognition, a very wide variety of features on the surface of a wafer, the wafer usually being bright-field illuminated and scanned with a camera (matrix or line camera).

An inspection apparatus of this kind of the KLA-Tencor Corporation is described in the article "Lithography Defects: Reducing and Managing Yield Killers through Photo Cell Monitoring," by Ingrid Peterson, Gay Thompson, Tony DiBiase, and Scott Ashkenaz, Spring 2000, Yield Management Solutions. The wafer inspection apparatus described therein works with an incident-light illumination device that examines microdefects with low contrast using a bright-field/dark-field illumination system.

For certain macrodefects, the aforesaid types of illumination do not produce enough contrast. In addition, the quality of the edge profile of features that are configured on the wafer, for example protrusions, conductor paths, etched depressions, or the like, cannot be adequately assessed.

SUMMARY OF THE INVENTION

It is the object of the present invention to create an apparatus for inspection of a wafer with which macrodefects can be determined with high contrast. A further intention is to create an apparatus for inspection of a wafer with which the quality of the edge profile of features configured on the wafer can be assessed reliably and in simple fashion.

This object is achieved by way of an apparatus for inspection of a wafer comprising: a wafer receiving device for receiving the wafer, wherein the wafer has a surface on which linearly extending features are configured, in a definable orientation, an image capture device for capturing an image of the surface in a dark-field arrangement, and at least two incident-light illumination devices that each radiate an illuminating light beam which is incident obliquely onto the surface of a wafer to be inspected and respectively defines an illumination axis, wherein the illumination axes are oriented perpendicular to one another, and the apparatus is designed in such a way that a projection of the respective illumination axis onto the surface of the wafer is oriented substantially perpendicular to respective linear features on the surface of the wafer.

According to the present invention, an apparatus for inspection of a wafer encompasses at least two incident-light illumination devices that each radiate an illuminating light beam which is incident obliquely onto a surface of a wafer to be inspected and defines a respective illumination axis, an image capture device for capturing an image of the surface of the wafer in a dark-field arrangement, and a wafer receiving device for receiving the wafer in a definable orientation. According to the present invention, the apparatus is characterized in that the illumination axes are oriented perpendicular to one another, and the apparatus is designed in such a way that a projection of the respective illumination axis onto the surface of the wafer is oriented substantially perpendicular to respective linear features on the surface of the wafer.

It is known that many features on the surface of wafers, for example conductor paths, etched depressions, or protrusions, extend substantially linearly. Because, according to the present invention, the light used for illumination of the surface of the wafer is incident perpendicular to the features extending on the surface of the wafer, defects that accumulate along the linear features as a result of process step errors, or that extend along the features or perpendicular to them, can be detected with particularly high contrast. With the apparatus according to the present invention it is possible to identify macrodefects of many different kinds, in particular macrodefects at protrusions or depressions or distortions on the surface of the wafer. The inventors have discovered that surface regions having no features or few features exhibit comparative few defects, whereas defects often accumulate in the vicinity of regions where the profile of the wafer's surface changes abruptly or discontinuously.

The illuminating light beams radiated by the at least two incident-light illumination devices are incident obliquely onto the surface of the wafer, and are thus reflected at a non-infinitesimal return angle relative to a normal line onto the surface of the wafer. The image capture device is arranged in a dark-field arrangement, so that the illuminating light reflected from the surface of the wafer is preferably completely blocked out of the image capture device, and the latter captures only scattered light deriving from an illuminated surface region. The captured image is preferably read out digitally and further processed. The incident-light illumination device can illuminate the entire surface of the wafer or definable portions on the surface of the wafer, for example portions encompassing dies or several dies. The image field of the image capture device preferably corresponds to the illuminated surface region.

The orientation in which the wafer to be inspected is received on the wafer receiving device can preferably be defined reproducibly. For that purpose, the wafer inspection apparatus can have associated with it a prealigner which determines the location of a notch or flat on the outer circumference of the wafer, aligns the wafer on the basis of the notch or flat, and then transfers it to the wafer receiving device while retaining the defined orientation. If the layout of the features to be configured on the wafer is known, the orientation of the illumination axis defined by the respective illuminating light beam can then be coordinated in such a way that its projection onto the surface of the wafer is aligned substantially perpendicular to the features extending linearly on the surface of the wafer.

While it is preferred that the aforementioned alignment of the respective illumination axis be performed within minimal tolerances, it has been found that with the apparatus according to the present invention, defects on the surface of the wafer can still be ascertained and assessed reliably and with high contrast even when the deviation from the ideal situation of a parallel or perpendicular orientation is as great as a few degrees, for example up to approximately 5°, more preferably only up to approximately 3°, and even more preferably only up to approximately 1° or a great deal less.

Using the apparatus according to the present invention it is also possible, in particularly preferred fashion, to assess the quality of the edge profile of features configured on the wafer. Because rounded edges of linear structures on the surface of the wafer act like a mirror for the illuminating light that is incident obliquely or in raking fashion, each layout possesses a characteristic pattern of reflected and scattered light. If that pattern changes in a batch of wafers, it is then easy, by means of the apparatus according to the present invention, to infer deviations from the reference edge profile defined by the layout.

The imaging axis defined by the image capture device is preferably oriented perpendicular to the surface of the wafer to be inspected, so that the dark-field arrangement is implemented by way of an oblique incidence of the illuminating light beam onto the surface. In principle, however, the imaging axis can also be inclined with respect to the surface of the wafer, provided the illumination angle is not equal to the imaging angle, since otherwise the dark-field arrangement could no longer be implemented. The image capture device is preferably arranged in stationary fashion relative to the surface of the wafer.

The illumination axis established by the incident-light illumination device, and the imaging axis established by the image capture device, preferably span a plane that is oriented perpendicular to the surface of the wafer. In this arrangement, the incident-light illumination device and the image capture device can be aligned in advantageously simple fashion. In principle, the aforesaid plane can also intersect the surface of the wafer at a different angle, up to a relative angle of only a few degrees. According to a further embodiment, the orientation of the plane spanned by the two axes relative to the surface of the wafer can also be modified by pivoting the illumination axis and/or the imaging axis, for example in order to vary the contrast during image capture.

To make the design of the apparatus even more flexible, the incidence angle $\alpha$ of the illuminating light beam can also be modified, a region on the surface of the wafer illuminated by the incident illuminating light beam preferably remaining stationary upon modification of the incidence angle so that, advantageously, the orientation of the image capture device does not need to be modified. Modification of the incidence angle $\alpha$ thus allows defects on the surface of the wafer to be identified and evaluated under different illumination conditions. Changing the incidence angle $\alpha$ makes it possible, in particular, to assess the quality of the edge profile of features configured on the wafer, and of defects present at edges, in advantageously simple fashion. At a certain incidence angle $\alpha$, for example, right-angle edges may ideally result in a relative low scattered-light intensity, whereas rounded edges deviating from the ideal right-angle shape may result only in an elevated scattered-light intensity or even in a directly reflected or diffracted light component, which is detected by the image capture device.

In order to modify the incidence angle $\alpha$, the respective incident-light illumination device can comprise an alpha-angle adjustment mechanism, for example a curved alignment rail along which the incident-light illumination device can be displaced, the radius of the alignment rail being coordinated with the distance between the incident-light illumination device and the incidence point of the illumination axis on the surface of the wafer in such a way that the illuminated region on the surface of the wafer remains stationary upon modification of the incidence angle.

The incidence angle can be varied over a wide range in the apparatus according to the present invention, for example in the range between approximately 3° and approximately 90°, more preferably in the range from approximately 20° to approximately 90°. Incidence angles in the range from approximately 40° to approximately 86° are particularly preferred according to the present invention. It should be noted, however, that a raking incidence of the illuminating light onto the surface of the wafer is also theoretically a possibility.

The apparatus according to the present invention encompasses at least two incident-light illumination devices. The illumination axes of the two incident-light illumination devices are oriented perpendicular to one another as seen in a plan view of the wafer, and the regions respectively illuminated by the incident-light illumination devices overlap one another. In this arrangement, defects or protrusions on the surface of the wafer that extend along the linearly extending features result in scattered or refracted light that derives from the illuminating light beams from both incidence directions.

According to another embodiment, the apparatus according to the present invention encompasses four incident-light illumination devices whose illumination axes, as seen in a plan view of the wafer, are orthogonal to one another and intersect one another in a region of the surface of the wafer. The incident-light illumination devices can be selectably switchable on and off.

The at least one incident-light illumination device can be a monochromatic light source, for example an LED or a linear LED arrangement, in which case a black-and-white image capture device can also be used. Preferably, however, the incident-light illumination device is a polychromatic light source, for example a flash light source or a linear flash light source arrangement, in which case the scattered light captured by the image capture device is detected and analyzed in spectrally resolved fashion.

For more homogeneous illumination of the surface of the wafer, a homogenization means can be provided in the respective beam path of the illuminating light beam. The homogenization means can be, for example, a diffusion disk or a microlens array.

According to a further aspect of the present invention, which can also be claimed separately and independently, the apparatus according to the present invention encompasses at least one imaging optical system that is associated with an incident-light illumination system in order to deflect the associated illuminating light beam in a different direction and image it appropriately onto the surface of the wafer. The imaging optical system can encompass refractive, diffractive, or reflective optical elements.

The imaging optical system is preferably designed also to make possible a certain spatial separation between the illumination system, imaging components, and image capture elements. According to a first embodiment, the imaging optical system encompasses a respective mirror in order to deflect the respective illuminating light beam in a different direction. Preferably, an oblique or raking incidence of the illuminating light beam is thereby implemented with no need to arrange imaging optical elements in the immediate vicinity of the wafer to be inspected. By means of suitable imaging optical elements arranged in the beam path of the illuminating light beam, the illuminating light beam can be shaped in such a way that an even more homogeneous illumination can be implemented. According to this embodiment, the incident-light illumination device can be aligned, in particular, perpendicular to the surface of the wafer, so that the base area of the apparatus according to the present invention can be reduced even further.

According to another embodiment, the imaging optical system encompasses in each case a periscope arrangement of mirrors having an inflected beam path in order to deflect a respective illuminating light beam in a different direction. The two mirrors of the periscope arrangement are preferably arranged parallel to one another and are pivotable and/or movable in coordination with one another, so that the incidence angle of the illuminating light beam incident onto the surface of the wafer can easily be modified. In this configuration the incident-light illumination device can also be oriented parallel to the surface of the wafer; this can offer advantages, for example, in terms of maintenance of the incident-light illumination device.

A separation panel can furthermore be provided in the context of the apparatus according to the present invention, at least one mirror being arranged below the separation panel in order to deflect the illuminating light beam onto the surface of the wafer. The incidence angle and the location of the illuminated region on the surface of the wafer can be modified by adjustment of the mirror arranged below the separation panel, for example by pivoting and/or vertical displacement. It is advantageous that with this embodiment, there is no need for arrangement of illumination devices in the immediate vicinity of the wafer, which could otherwise easily result in damage to the wafer surface and problems in aligning the illuminating light beam. The illumination devices can instead be arranged at a different suitable position in or outside the apparatus.

Preferably the wafer can be arranged below the separation panel, and the at least two incident-light illumination devices and/or the image capture device are arranged above the separation panel. In this configuration, the mirror arranged below the separation panel can be held in stationary fashion, and an alignment of the illuminating light beams can be brought about exclusively by adjusting optical elements arranged above the separation panel. It is advantageous that the apparatus according to the present invention can be aligned more easily and more reliably, and that even more favorable conditions can be created for the installation, maintenance, and operation of the apparatus.

The apparatus is thus subdivided into a first level and a second level offset vertically with respect to the first level; the wafer, which is comparatively sensitive to contaminants, can be arranged in the first level, and the less-sensitive at least two incident-light illumination devices and/or the image capture device are arranged in the second level.

An image capture device that encompasses an objective and a linear or matrix camera is preferably used for the inspection of macrodefects. For automatic inspection of the surface of the wafer, the apparatus according to the present invention is connected to a data readout device, for example a computer or frame grabber, which sequentially reads out the image data of the linear or matrix camera. Parameters or defects of the wafer can then be determined from the image data that are read out. In particular, the evaluation of defects on the surface of the wafer can also be performed in spatially resolved fashion, for which purpose the data from the data readout device are coordinated, for example, with respect to markings on the surface or at the edge of the wafer.

BRIEF DESCRIPTION OF THE DRAWINGS

The invention will be described below by way of example and with reference to the appended Figures, from which further features, advantages, and objects to be achieved may be inferred. In the Figures.

In the Figures, identical reference characters designate identical or identically functioning elements or assemblies.

DETAILED DESCRIPTION OF THE INVENTION

Figure 1:
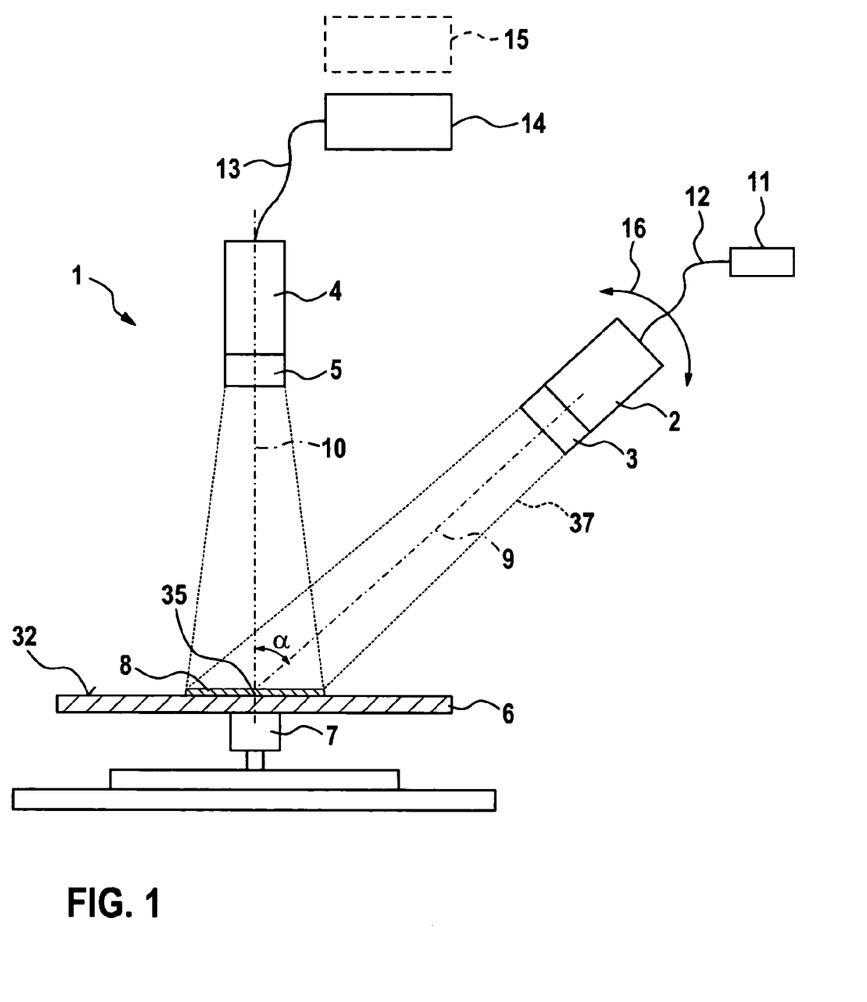
FIG. 1 is a cross section through the apparatus according to the present invention.

FIG. 1 shows, in a schematic cross section, a wafer inspection apparatus 1 according to the present invention. It encompasses an incident-light illumination device 2 that defines an illumination axis 9 which intersects surface 32 of wafer 6 at incidence point 35, a camera 4 serving as image capture device, and a wafer receiving device 7 that holds wafer 6 in either stationary or rotatable fashion. Wafer 6 is vacuum-suctioned onto wafer receiving device 7. Incident-light illumination device 2 comprises an imaging optical element 3, for example a lens or objective, that shapes illuminating light beam 37 in such a way that illuminating light beams 37, incident in inclined fashion onto surface 32 of wafer 6 to be inspected, illuminate a corresponding region 8 that covers the entire surface of wafer 6 or a subregion thereof, for example individual dies.

Camera 4 is perpendicular to surface 32 of wafer 6 and defines an imaging axis 10 that intersects surface 32 of wafer 6 at incidence point 35. An objective 5 is arranged at the front end of camera 4 so that illuminated region 8 is imaged into camera 4. Imaging axis 10 and illumination axis 9 span a plane that is orthonormal to surface 32 of wafer 6. In principle, this plane can also intersect surface 32 of wafer 6 at a different angle.

In FIG. 1, camera 4 and incident-light illumination device 2 are arranged in a dark-field arrangement, so that what is imaged into camera 4 is not illuminating light reflected directly from surface 32 of wafer 6, but only scattered or diffracted light deriving from defects on surface 32 of wafer 6 in illuminated region 8. As FIG. 1 shows, illumination axis 9 is inclined with respect to surface 32 of wafer 6. Illumination axis 9 encloses with imaging axis 10 an incidence angle α that corresponds, in the example depicted, to a normal line onto surface 32 of wafer 6. Incidence angle α is selected as appropriate; this can also be dependent on the features to be configured on wafer 6. Although incidence angle α can in principle be varied over a wide range, e.g. from 3° to approximately 90° and more preferably from approximately 20° to approximately 90°, it is preferred if illuminating light beam 37 strikes surface 32 of wafer 6 at an incidence angle α in the range from approximately 40° to approximately 86°.

As indicated by double arrow 16, incident-light illumination device 2 can also be held pivotably, so that the incidence angle α can be adapted to the particular wafer 6 to be inspected. To modify the incidence angle α, an alpha adjustment mechanism (not depicted) can be provided which is designed so that upon modification of the incidence angle α, illuminated region 8 on surface 32 of wafer 6 remains substantially stationary. The alpha adjustment mechanism (not depicted) can have for that purpose, for example, a curved alignment rail whose radius is coordinated with the distance between incident-light illumination device 2 and incidence point 35 in such a way that incidence point 35 remains substantially stationary upon pivoting of incident-light illumination device 2.

A light source can be provided directly in incident-light illumination device 2. As depicted in FIG. 1, incident-light illumination device 2 can also encompass an external light source 11 whose light is coupled into the beam path via a light guide bundle 12. Light source 11 can be a monochromatic or polychromatic light source. LEDs or linear LED arrangements are especially suitable as monochromatic light sources. Flash lamps, white light LEDs, and the like are especially suitable as polychromatic light sources. Light source 11 can be operated continuously. Preferably, however, light source 11 is operated in timed fashion, for example as flash light that is triggered synchronously with image acquisition.

In very particularly preferred fashion, linear fiber illuminators, whose light is radiated in linear fashion and spread with a cylindrical lens, are used as incident-light illumination device 2.

Camera 4 is connected via a data line 13 to a data readout device 14 that evaluates the captured image data or temporarily stores them, e.g. for later image evaluation. Data readout device 14 is preferably a computer having a frame grabber that reads out the lines of a CCD camera 4 periodically or in timed fashion, for example synchronously with the triggering of the flash light. The image data that are read out can also be displayed on monitor 15, or displayed there after evaluation by means of suitable software.

Figure 2:
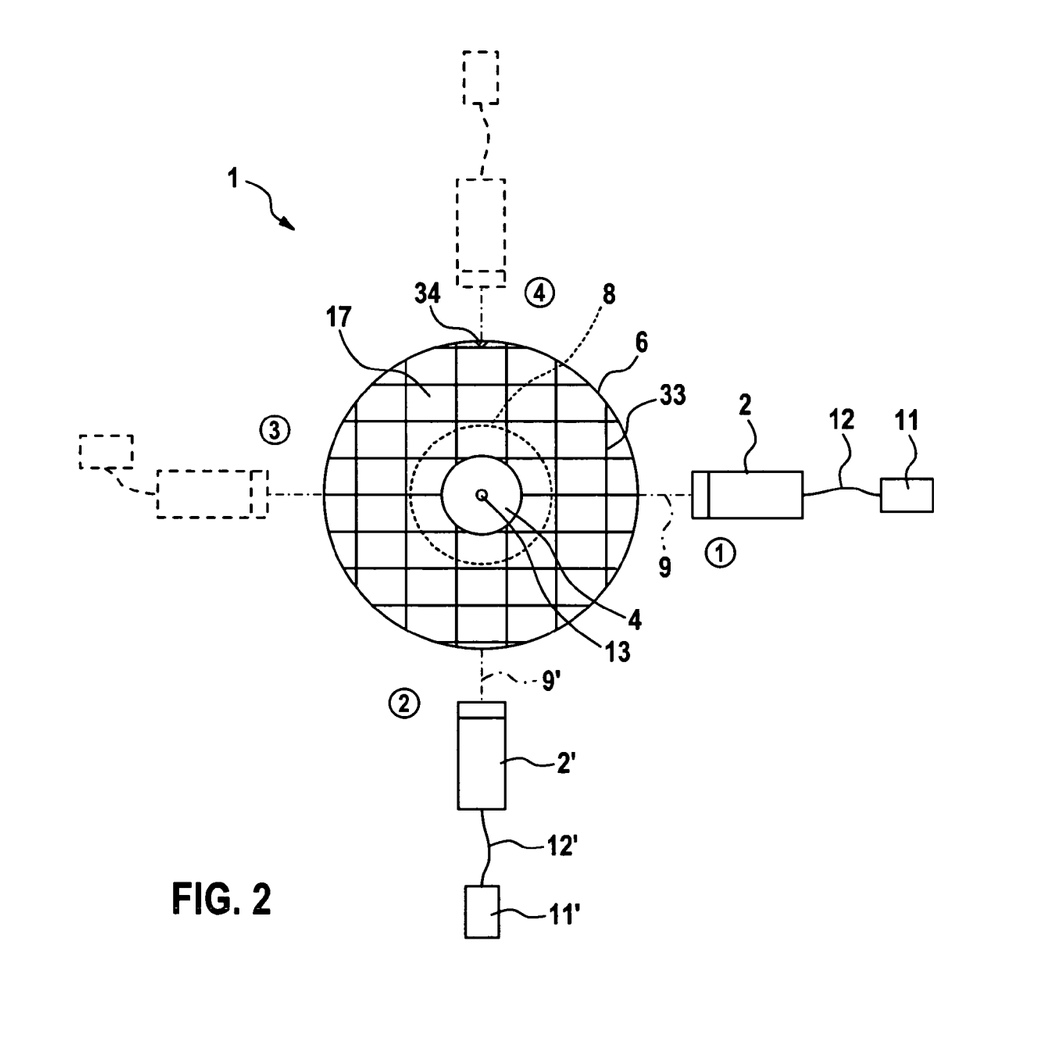
FIG. 2 is a plan view of the apparatus according to FIG. 1.

FIG. 2 shows wafer inspection apparatus 1 according to FIG. 1 in a schematic plan view. As depicted in FIG. 2, wafer inspection apparatus 1 encompasses two incident-light illumination devices 2, 2' that are oriented at right angles to one another. The light of light source 11, 11' is coupled via respective light guide bundles 12, 12' into the respective incident-light illumination device 2, 2'. As depicted in FIG. 2, wafer 6 is held in a definable orientation in wafer inspection apparatus 1.

As depicted in FIG. 2, linearly extending features 33, are configured on the surface of wafer 2, extending in one direction or in two mutually orthogonal directions. In the latter case the surface of wafer 6 is thus subdivided into rectangular subregions 17, that correspond, for example, to one die. A notch 34 or a flat, which serves for orientation of wafer 6, is provided on the circumferential edge of wafer 6. All the process steps for configuring features on wafer 6 are performed, as is known, with wafer 6 in a defined orientation. Because the layout of the structures to be configured is known, the manner in which linear features 33 extend can be inferred unequivocally from the location of the flat or notch 34 on the circumferential edge of wafer 6. Wafer 6 can in turn be oriented in predefinable fashion by means of a prealigner. Notch 34 is located at the top in FIG. 2. The prealigner (not depicted) can be a component of wafer inspection apparatus 1 or can be positioned upstream from wafer inspection apparatus 1, in which case wafer 6 is transferred to wafer inspection apparatus 1 with a definable orientation.

As depicted in FIG. 2, wafer 6 is transferred to wafer receiving device 7 (FIG. 1) in such a way that the projections of illumination axes 9, 9' onto the surface of wafer 6 extend substantially perpendicular to linear features 33 on surface 32 of wafer 6. Slight deviations from the ideal situation of an exactly perpendicular orientation of illumination axes 9, 9' with respect to linear features 33 are possible according to the present invention; for example, the misalignment can be up to approximately 5°, more preferably only up to approximately 3°, and even more preferably only up to approximately 1° or very much less.

As indicated by the dashed lines in FIG. 2, several possibilities exist for arranging two incident-light illumination devices 2 around wafer 6 in such a way that the projections of the respective illumination axes onto the surface of wafer 6 are oriented substantially perpendicular to linear structures 33 on the surface of wafer 6. In principle, four incident-light illumination devices 2, having mutually orthogonal illumination axes 9 orthogonal to one another as seen in a plan view of wafer 6 and capable of being selectively activated, can also be arranged around wafer 6 at the positions labeled with the numbers 1 through 4. According to the present invention, the two illuminating light beams can be incident mutually orthogonally or oppositely to one another, in projection onto the surface of wafer 6, if only two incident-light illumination devices 2 are used. It is important to ensure that region 8 illuminated by one respective incident-light illumination device 2 sufficiently, preferably substantially completely, overlaps region 8 illuminated by a different incident-light illumination device 2'.

According to the present invention, the geometry used is one with two incident-light illumination devices 2, 2' that radiate onto the surface of wafer 6 in such a way that the projections of illumination axes 9, 9' onto surface 32 of wafer 6 extend mutually orthogonally and intersect at an incidence point where imaging axis 10 of camera 4 also intersects the surface of wafer 6.

As a result of the alignment according to the present invention of illumination axes 9, 9' relative to linear features 33 on the surface of wafer 6, two preferred directions are defined that make possible even more reliable inspection of the surface of the wafer. This is because it may be assumed that the defects on the surface of the wafer accumulate, in particular, wherever the profile of the surface changes abruptly or discontinuously, i.e. in particular along linear features 33.

According to the present invention, this arrangement of defects corresponds to the preferred directions defined by the illumination arrangement.

Surface 32 of wafer 6 is usually inspected only with a fixed incidence angle α. Alternatively, if a motor-driven alpha adjustment mechanism is provided, surface 32 of wafer 6 can also be inspected at several incidence angles α. Data evaluation is accomplished automatically in computer 14 by means of suitable software.

Figure 3:
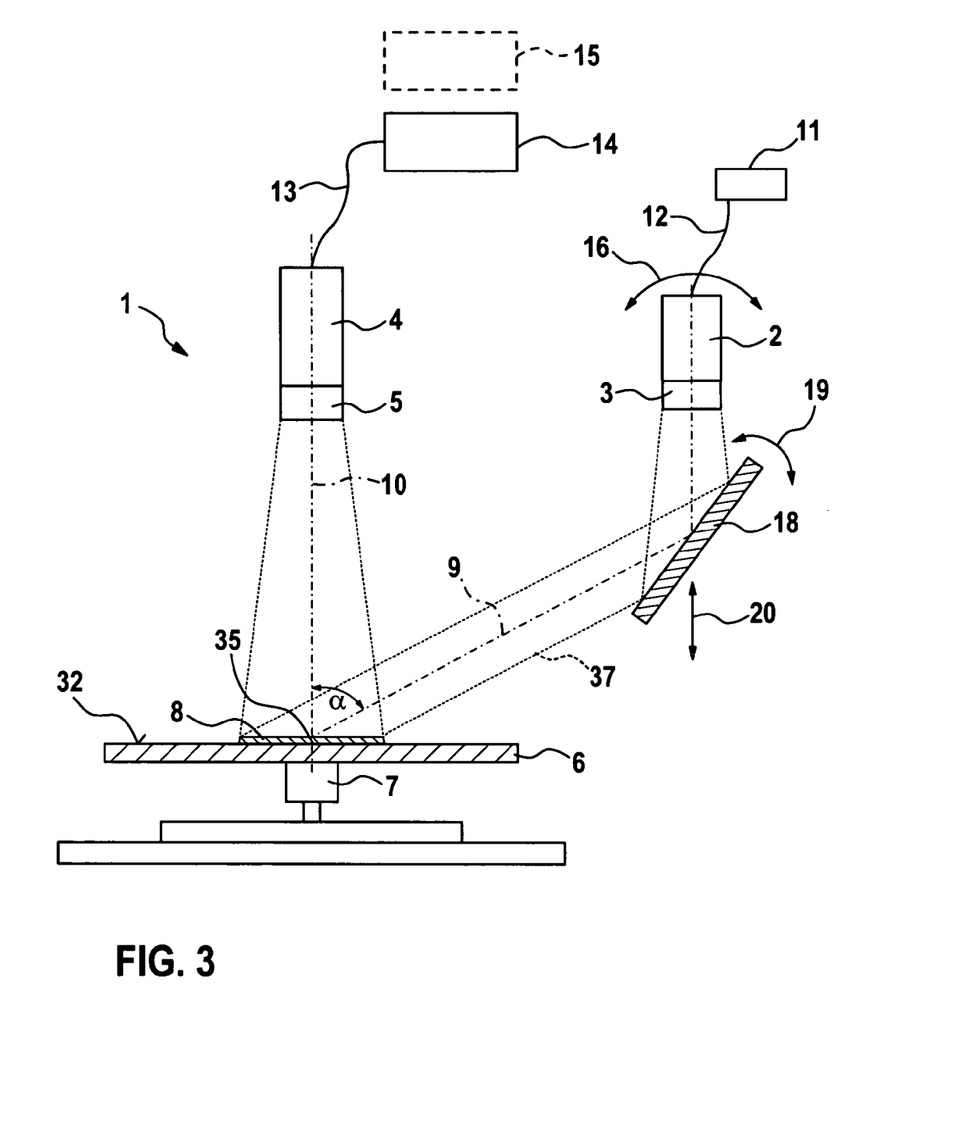
FIG. 3 is a cross section through a further embodiment according to the present invention, having a deflection mirror.
Figure 4:
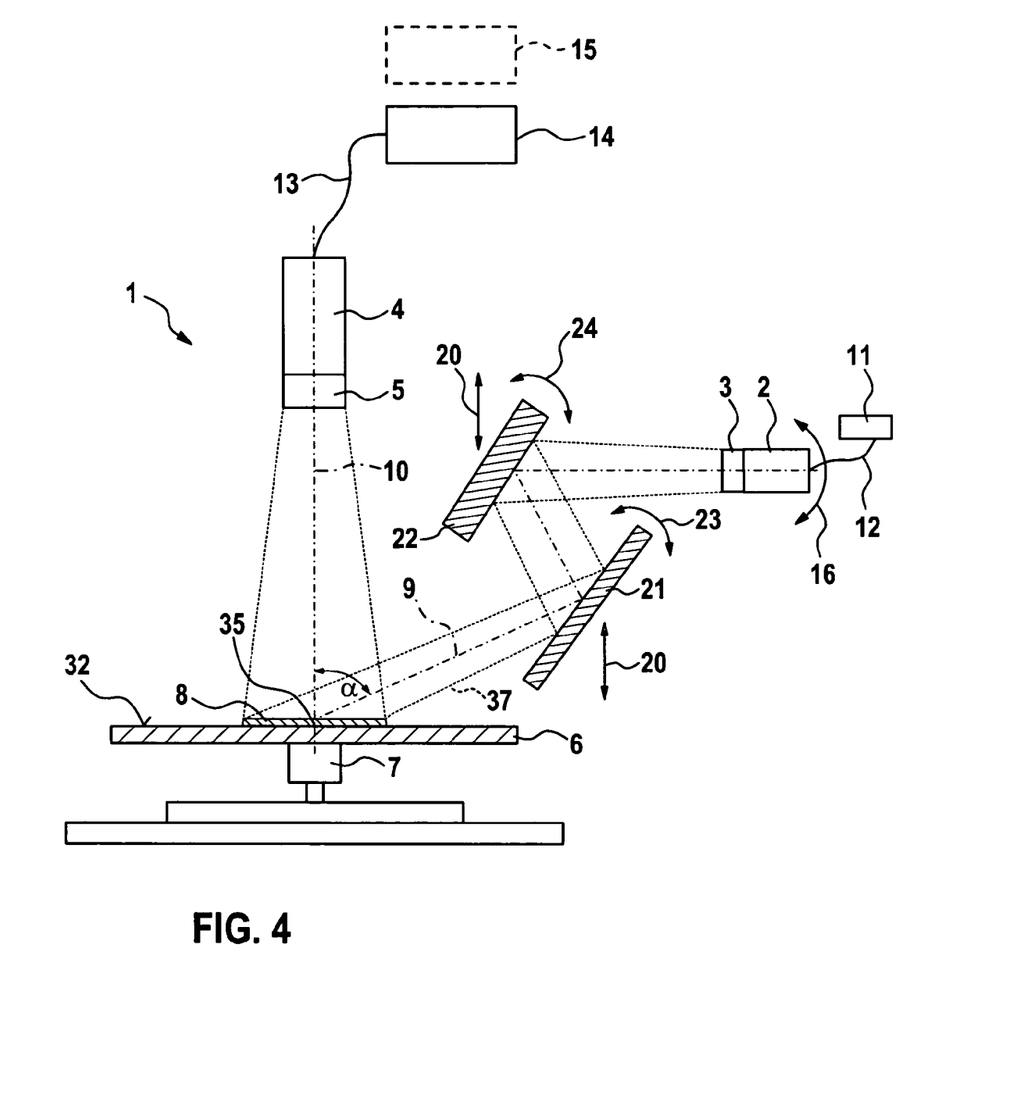
FIG. 4 is a cross section through a further embodiment according to the present invention, having a periscope arrangement of deflection mirrors.
Figure 5:
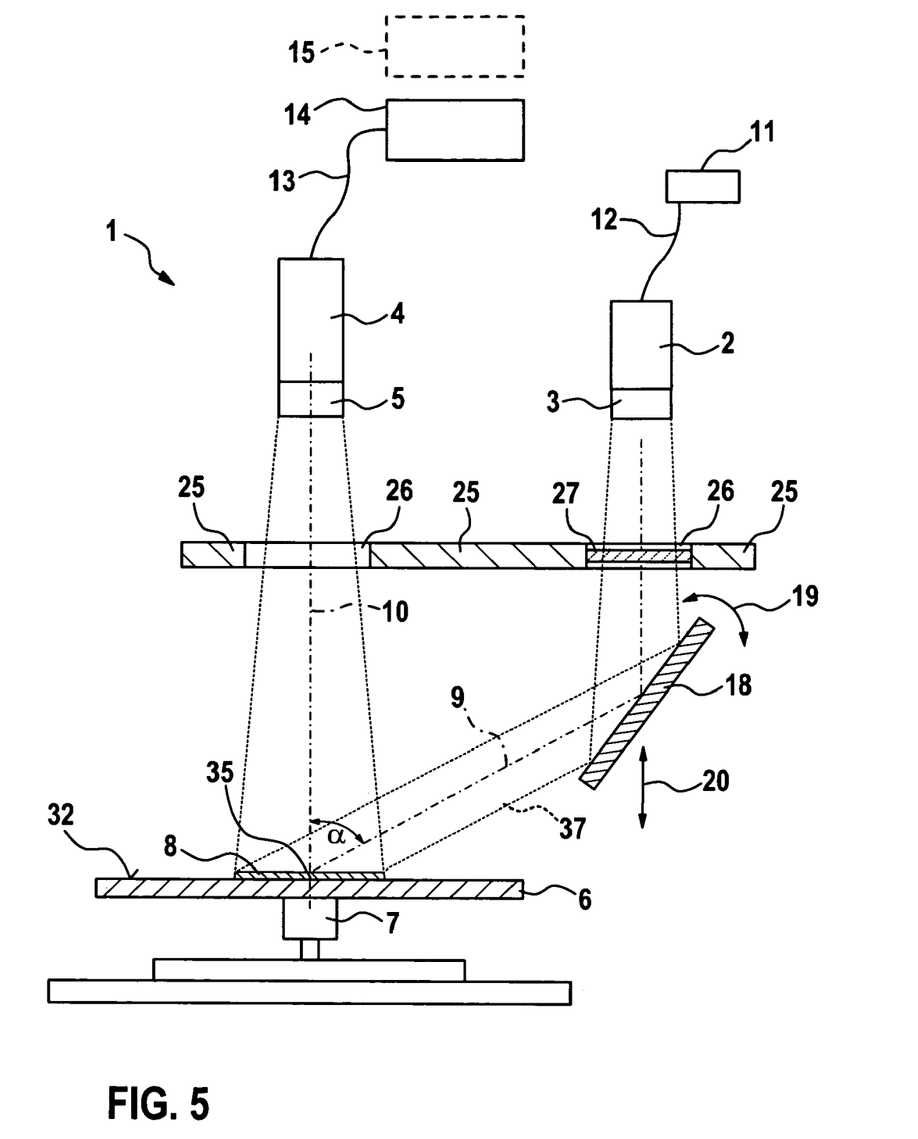
FIG. 5 is a cross section through a further embodiment according to the present invention, having a separation panel for subdividing the apparatus into two levels offset vertically from one another.

FIGS. 3 through 5 show further embodiments of wafer inspection apparatus 1, in which illuminating light beam 37 is deflected. According to FIG. 3, incident-light illumination device 2 is oriented substantially orthogonally with respect to surface 32 of wafer 6, and illuminating light beam 37 is imaged via a deflection mirror 18 onto surface 32 of wafer 6. As indicated by double arrows 19, 20, the position and orientation of deflection mirror 18 can be varied, with the result that incidence angle α can easily be modified. Deflection mirror 18 can be arranged, in particular, in the immediate vicinity of the circumferential edge of wafer 6, so that even comparatively large incidence angles α, up to almost 90 degrees, can readily be implemented. As indicated by double arrow 16, the incident-light illumination device can also be pivoted.

According to FIG. 4, a periscope arrangement of two deflection mirrors 21, 22 that appropriately folds the beam path of the illuminating light beam is provided. As depicted in FIG. 4, incident-light illumination device 2 is oriented substantially parallel to surface 32 of wafer 6. As indicated by double arrows 20, 23, deflection mirrors 21, 22 can be pivoted independently or in coordination with one another. As indicated by double arrow 16, incident-light illumination device 2 can also be pivoted about its longitudinal axis. As a result of this arrangement, the incidence angle α and the spreading of illuminating light beam 37 can easily be modified.

Other optical elements, for example diffractive or refractive optical elements, are of course also suitable for deflection of the illuminating light beam. It is also possible to provide an imaging optical system in the beam path from illuminated region 8 to camera 4, so that camera 4 can also be arranged farther away or in a different orientation with respect to wafer 6.

A beam deflection system as shown in FIGS. 3 and 4 can also be used for a spatial subdivision of the wafer inspection apparatus. This is depicted schematically in FIG. 5, where wafer inspection apparatus 1 comprises a deflection mirror 18 that can be held, and also displaced or pivoted, in the manner described in conjunction with FIG. 3.

Arranged above deflection mirror 18 is a panel 25 that has two openings 26 for the illuminating light beam and the imaging light beam. Transparent panels 27; imaging optical elements such as lenses; or diffusion disks, microlens arrays, or the like serving as homogenization means, can be arranged in openings 26. As shown in FIG. 5, most of the other elements of wafer inspection apparatus 1, including incident-light illumination device 2, imaging optical element 3, objective 5, and camera 4, are arranged above panel 25. Panel 25 can also, of course, be used with the periscope arrangement of mirrors depicted in FIG. 4. In a configuration of this kind (not depicted), the panel is preferably arranged between mirrors 21, 22 (FIG. 4), in which context lower mirror 21 can then also be held in stationary fashion, while upper mirror 22 is preferably held in pivotable and/or displaceable fashion so that the alignment of illuminating light beam 37 can be modified.

Wafer inspection apparatus 1 as a whole is subdivided by panel 25 into two levels vertically offset from one another, substantially only wafer 6 and wafer receiving device 7 being arranged in the lower level, while the most important optical elements, the light sources, and the camera for image capture are arranged in the level located vertically thereabove. This spatial subdivision of wafer inspection apparatus 1 offers new possibilities in terms of its design, which may result in lower costs and more advantageous maintenance and repair, and in even more advantageous operation. The effort required for alignment of wafer inspection apparatus 1 can also be decreased.

Figure 6:
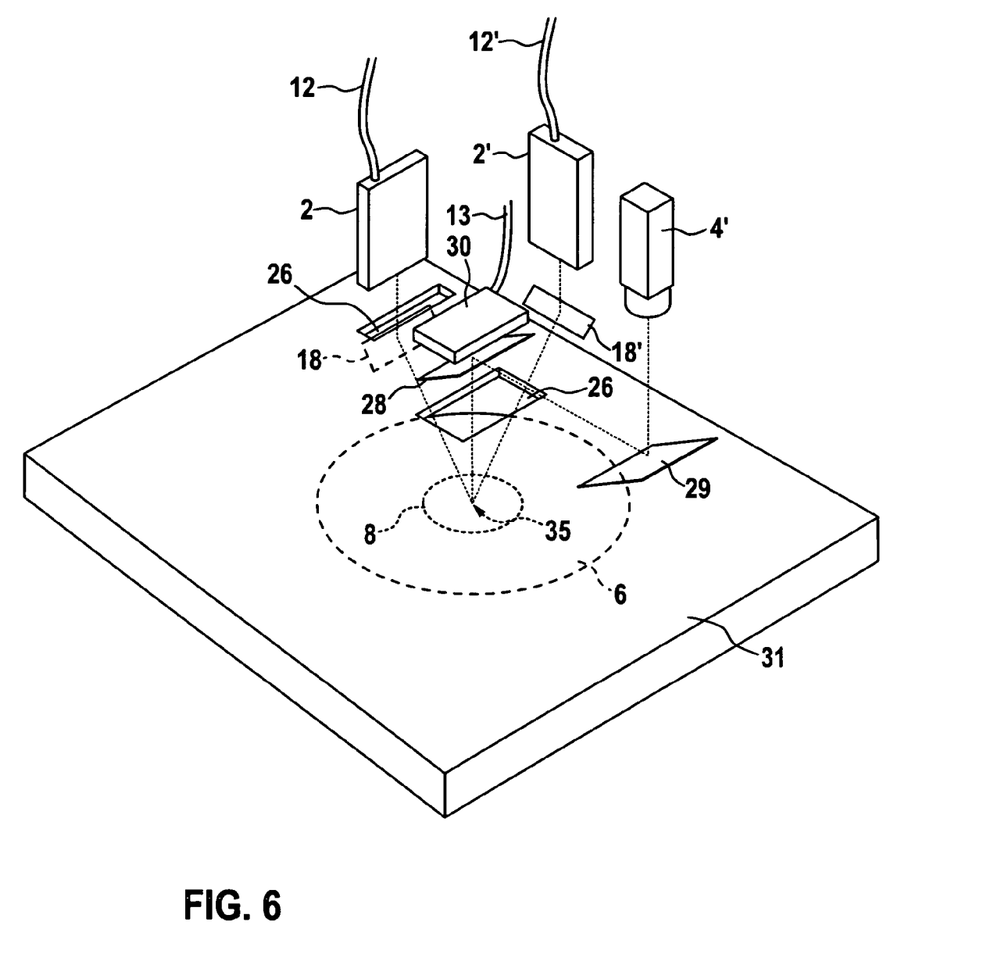
FIG. 6 is a perspective view of a further embodiment according to the present invention.

FIG. 6 shows, in a perspective arrangement, a further embodiment of a wafer inspection apparatus 1. All the elements are placed on a mounting plate 31. Incident-light illumination devices 2, 2' are oriented perpendicular to the surface of the wafer (not depicted). The respective illuminating light beams are imaged onto the surface of the wafer at a raking incidence angle via deflection mirrors 18, 18'. Camera 4' is also oriented perpendicular to the surface of the wafer. The light scattered in the illuminated region on the surface of the wafer is imaged via semitransparent mirror 28 and deflection mirror 29 into camera 4'. Located above semitransparent mirror 28 is a large-area illuminator 30 that can be used for other inspection methods. As a result of the perpendicular arrangement of incident-light illumination device 2, 2' and camera 4', the base area of wafer inspection apparatus 1 is advantageously small.

Although not depicted in the Figures described above, wafer inspection apparatus 1 according to the present invention encompasses a movable stage, for example an X-Y displacement stage, so that the entire surface 32 of wafer 6 can be scanned by suitable displacement of wafer 6. The wafer inspection apparatus according to the present invention is suitable in particular for assessing the edge profile of features extending linearly on the surface of the wafer.

What is claimed is:

1. An apparatus for inspection of a wafer, comprising:
   a wafer receiving device for receiving the wafer, wherein the wafer has a surface on which linearly extending features are configured, in a definable orientation,
   an image capture device for capturing an image of the surface in a dark-field arrangement, and
   at least two incident-light illumination devices that each radiate an illuminating light beam which is incident obliquely onto the surface of a wafer to be inspected and respectively defines an illumination axis,
   wherein the illumination axes are oriented perpendicular to one another, and the apparatus is designed in such a way that a projection of the respective illumination axis onto the surface of the wafer is oriented substantially perpendicular to respective linear features on the surface of the wafer.

2. The apparatus as defined in claim 1, in which an imaging axis established by the image capture device is oriented perpendicular to the surface of the wafer.

3. The apparatus as defined in claim 2, in which one of the illumination axes and the imaging axis span a plane that is oriented perpendicular to the surface of the wafer.

4. The apparatus as defined in claim 1, in which an incidence angle of one of the illuminating light beams is modifiable, wherein an illuminated region on the surface of the wafer remains stationary when the incidence angle is modified.

5. The apparatus as defined in claim 4, in which the incidence angle lies in a range from approximately 3° to approximately 90°.

6. The apparatus as defined in claim 5, in which the incidence angle lies in a range from approximately 20° to approximately 90°.

7. The apparatus as defined in claim 6, in which the incidence angle lies in a range from approximately 40° to approximately 86°.

8. The apparatus as defined in claim 1, wherein at least one further incident-light illumination device is arranged in such a way that two illumination axes are oriented parallel to one another, such that regions on the surface of the wafer that are respectively illuminated by the incident-light illumination devices overlap one another.

9. The apparatus as defined in claim 1, wherein four incident-light illumination devices are provided such that illumination axes of one pair of the incident-light illumination devices are orthogonal to each other and illumination axes of another pair of incident-light illumination devices are orthogonal to each other, and the illumination axes of the four incident-light illumination devices intersect in a region on the surface of the wafer that is imaged into the image capture device.

10. The apparatus as defined in claim 1, wherein at least one incident-light illumination device encompasses a monochromatic light source.

11. The apparatus as defined in claim 1, wherein at least one incident-light illumination device encompasses a polychromatic light source, and the image capture device captures an image of the surface of the wafer in spectrally resolved fashion.

12. The apparatus as defined in claim 11, in which the polychromatic light source is a flash light source or a linear flash light source arrangement.

13. The apparatus as defined in claim 1, wherein each incident-light illumination device respectively encompasses a light guide bundle and an associated imaging optical element.

14. The apparatus as defined in claim 1, wherein a homogenization means for homogenizing each respective illuminating light beam is provided.

15. The apparatus as defined in claim 1, wherein at least one imaging optical system is associated with at least one of the incident-light illumination devices in order to image the associated illuminating light beam onto the surface of the wafer.

16. The apparatus as defined in claim 15, wherein the imaging optical system encompasses a mirror in order to deflect the illuminating light beam of the at least one of the incident-light illumination devices in a different direction, wherein the at least one of the incident-light illumination devices is oriented perpendicular to the surface of the wafer.

17. The apparatus as defined in claim 16, wherein the imaging optical system encompasses a periscope arrangement of mirrors in order to deflect the illuminating light beam of the at least one of the incident-light illumination devices in a different direction, wherein the at least one of the incident-light illumination devices is oriented parallel to the surface of the wafer.

18. The apparatus as defined in claim 16, wherein the mirror is held pivotably and/or displaceably.

19. The apparatus as defined in claim 1, wherein the wafer is transferable in aligned fashion to the wafer receiving device, or is alignable thereon.

20. The apparatus as defined in claim 1, wherein a separation panel is provided, wherein at least one mirror is arranged below the separation panel in order to deflect at least one of the illuminating light beams onto the surface of the wafer.

21. The apparatus as defined in claim 20, wherein the separation panel has at least one opening so that the at least one of the illuminating light beams, and/or light from the surface of the wafer, can pass through the separation panel.

22. The apparatus as defined in claim 20, wherein the wafer can be arranged below the separation panel and the at least two incident-light illumination devices and/or the image capture device are arranged above the separation panel.

23. An apparatus for inspection of a wafer, comprising:
a wafer receiving device for receiving the wafer, wherein the wafer has a surface on which linearly extending features are configured, in a definable orientation,
an image capture device for capturing an image of the surface in a dark-field arrangement, and
at least two incident-light illumination devices that each radiate an illuminating light beam which is incident obliquely onto the surface of a wafer to be inspected and respectively defines an illumination axis,
wherein the illumination axes are oriented perpendicular to one another, and the apparatus is designed in such a way that a projection of the respective illumination axis onto the surface of the wafer is oriented substantially perpendicular to respective linear features on the surface of the wafer, an imaging axis established by the image capture device is oriented perpendicular to the surface of the wafer and a separation panel is provided,
wherein at least one mirror is arranged below the separation panel in order to deflect at least one of the illuminating light beams onto the surface of the wafer.

* * * * *